United States Patent [19]

Woo

[11] 4,019,365
[45] Apr. 26, 1977

[54] THERMOMECHANICAL ANALYZER
[75] Inventor: Lecon Woo, Newark, Del.
[73] Assignee: E. I. Du Pont de Nemours and Company, Wilmington, Del.
[22] Filed: Mar. 4, 1975
[21] Appl. No.: 553,453
[52] U.S. Cl. .................................. 73/15.6; 73/95.5
[51] Int. Cl.² ....................................... G01N 3/18
[58] Field of Search ............ 73/15.6, 95, 95.5, 160; 33/147 D, 148 D

[56] References Cited
UNITED STATES PATENTS

| | | | |
|---|---|---|---|
| 2,416,664 | 2/1947 | Ruge | 33/147 |
| 2,588,630 | 3/1952 | Jackman | 33/148 |
| 2,685,195 | 8/1954 | Streblow | 73/15.6 |
| 2,732,708 | 1/1956 | Linhorst | 73/94 X |
| 2,922,302 | 1/1960 | Kernam | 73/94 X |
| 3,075,378 | 1/1963 | Bernard et al | 73/15.6 |
| 3,397,572 | 8/1968 | Stolz et al. | 73/15.6 |
| 3,614,834 | 10/1971 | Holt et al. | 33/147 |
| 3,813,919 | 6/1974 | Taniguchi et al. | 73/15.6 |

OTHER PUBLICATIONS

Bernstein et al. "Stress Relaxation with Finite Strain", in Trans. Soc. of Rheology, vol. 7, 1963, pp. 400 & 401.

*Primary Examiner*—Herbert Goldstein

[57] ABSTRACT

A thermomechanical analyzer is adapted to measure stress or strain in a sample material by the use of a flat, passive spring, having a known modulus of elasticity, in conjunction with an axially displaceable shaft which mechanically links the spring and the sample together. The linkage is such that the sample under test and the spring are mechanically connected in parallel, i.e., each undergo equal displacement. A transducer senses axial displacement of the shaft such that the magnitude of the shaft displacement is related to the stress in the sample. The sample may be subjected to temperature variations during the test cycle.

11 Claims, 5 Drawing Figures

THERMOMECHANICAL ANALYZER

BACKGROUND OF THE INVENTION

This invention relates to a mechanical analyzer, and, more particularly, to a thermomechanical analyzer for ascertaining certain physical and chemical characteristics of materials.

In the manufacture and use of materials, particularly organic materials, it is necessary to obtain such information as the materials softening temperature, tensile modulus, shrink temperatures, glass transistion temperature, elastic modulus, and the like. Accordingly, it has become customary to ascertain this information and characterize various materials by the results of various mechanical property measurements including thermomechanical analysis. Measurements of this type find wide use, for example, on polymeric materials including fibers, yarns and films. In one instance, by measuring the relationship between temperature and the retractive force exerted by a fiber (and the resulting stress or tension if the fiber's cross-section area is known) one can obtain an indication of the structural changes occurring in the fibers as a function of temperature. Such property controls the use to which a fiber can be put. In the case of acrylic yarns, for example, the orientation and state of internal stress in the typing molecules tend to control the physical properties of the yarn itself.

The glass transistion temperature of a polymer fiber is another property that is particularly useful in characterizing the fiber. Such temperature is useful in determining the conditions under which drawing, texturing, annealling, dying, fiber softening, crystallization and other properties can take place. Such temperature may be used in the prediction of the dyeability of the fiber.

A conventional means for measuring shrinkage tension, which is the retractive force exhibited, of yarn or other elongated material when heated, involves mounting a looped specimen of the yarn between hooks in a small oven provided with a heater and a temperature sensor. One hook is attached to a tension gage having an electrical output indicative of load or force and the other is positioned at a distance which permits a taut loop. The oven temperature is then increased at a programmed rate and the temperature in the oven measured and fiber tension or stress plotted on a graph as a function of temperature. As is known, many yarns in the lower temperature ranges show single or multiple peaks in the tension/temperature plot. The location and magnitude of the peak(s) characterizes the yarn and its mechanical and thermal history.

Another desirable measurement is that of stress relaxation measurement of plastics. A standard test for such measurement is described in ASTM specification D-2991-71. According to this test, a piece of plastic is placed between two gripping members and the time dependent change in the stress which results from the application of a constant total strain to the specimen at a constant temperature is obtained. The electrical outputs of a load cell and extensometer are recorded as a function of time and the stress calculated which is then plotted as a function of time.

A disadvantage of all of these prior art techniques involves the use of an active load cell as well as the use of an extensometer for measuring displacement of the sample under load conditions whether generated internally or externally. This requires the utilization of specific instrumentation apparatus having in most instances only a single use. Furthermore, load cells (particular double element cells) are in many cases subject to failure in that the use of one more active element increases the chances of such failure. Also such cells often tend to be noisy and increase the measurement error.

A thermomechanical analyzer is described in U.S. Pat. No. 3,474,658, issued Oct. 28, 1969 to Levy et al. There is described in the said Levy patent a thermomechanical analyzer capable of accurately measuring displacement of material samples under various temperature and load conditions. This analyzer uses a vertical shaft slideably mounted therein and has a probe attached to the shaft at one end to act on the sample. Since the Levy et al. analyzer is a highly sensitive and accurate unit, it would be highly desirable to provide it with an attachment such that it could measure stress/tension as well.

Accordingly, it is the object of this invention to provide an improved stress measuring device.

Another object of this invention is to provide an improved stress measuring method.

A further object of this invention is to provide an improved method of converting a displacement transducer into a stress measuring device.

An additional object of this invention is to provide an improved stress-tension measuring device utilizing a passive element.

SUMMARY OF THE INVENTION

According to the method of this invention a spring having a known modulus of elasticity is used to measure the stress in a sample under various temperature and/or load conditions. A first portion of both the spring and the sample are secured to a fixed reference point. Next a second portion of both the spring and the sample are interconnected such that they are mechanically in parallel. The displacement of the spring caused by the sample under different load or temperature conditions is a measure of the stress of the sample.

A mechanical analyzer for measuring stress or tension in a sample material is constructed to include an elastic means having a known modulus of elasticity over the measuring range of the analyzer, a coupling means for mechanically coupling the elastic means and the sample mechanically parallel such that each are subjected to the same linear displacement, and transducer means for sensing the linear displacement. By this arrangement, the requirement of an active load cell is eliminated. Stresses in the sample may be measured in a preferred embodiment by a simple modification of an existing displacement tranducer by the simple addition of a passive spring element thereto.

BRIEF DESCRIPTION OF THE DRAWINGS

The embodiments of this invention and their advantages can be more readily understood by referring to the accompanying drawings in which.

DESCRIPTION OF THE PREFERRED EMBODIMENT

Figure 1:
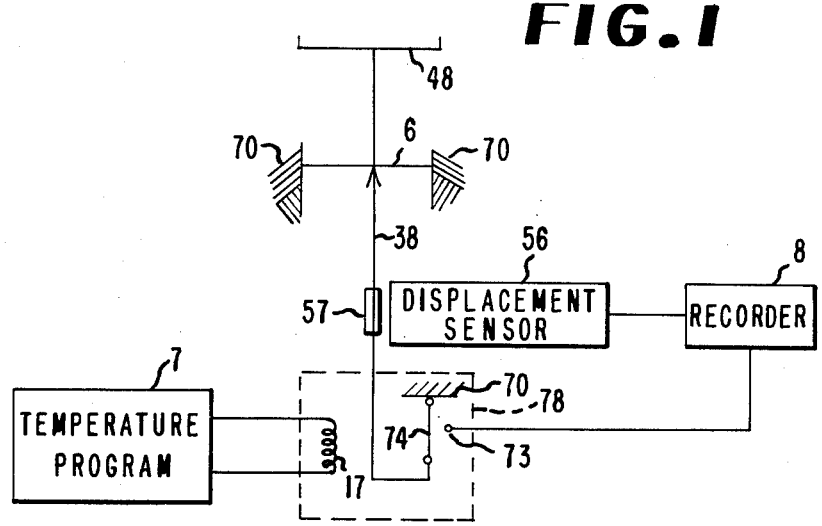
FIG. 1 is a block schematic diagram depicting the elements of a mechanical analyzer system constructed in accordance with this invention.

The block schematic diagram of FIG. 1 depicts the functional operation of a mechanical analyzer constructed or modified in accordance with this invention. The sample under test is in this case depicted as a piece of fiber or film 74. As will be described, the analyzer of this invention can measure stress in samples generated either internally or externally of the sample either as a function of time or temperature. The value of these measurements in ascertaining the physical properties of the sample as well as its processing history has been noted hereinbefore.

Figure 3:
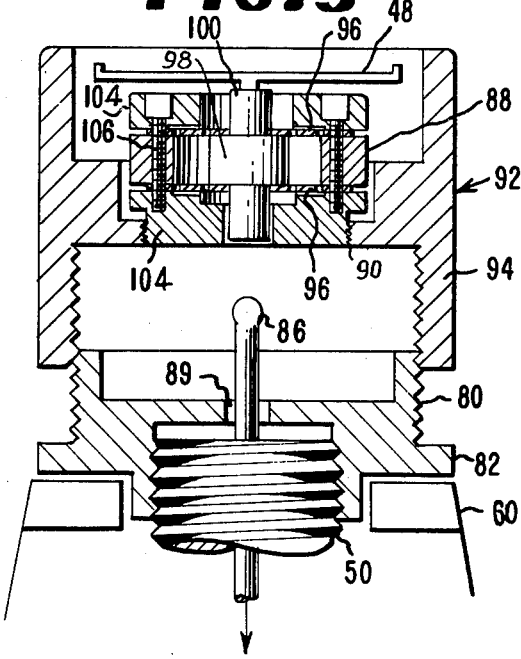
FIG. 3 is a partially schematic, partially cut away representation of the modification attachment for the thermomechanical analyzer illustrated in FIG. 2 which permits its conversion into the stress-strain analyzer of this invention.

The mechanical arrangement of the analyzer will be described in connection with FIGS. 2 and 3 as a modification to an existing thermomechanical analyzer, Model No. 942, sold by E. I. duPont de Nemours and Company, Wilmington, DE. According to this invention, an elastic means or spring 6, FIG. 1, depicted in the form of a flat spring having a known modulus of elasticity at least throughout its desired operating range is coupled through a linkage or shaft 38 to a sample 74 of material under test such that the spring 6 and the sample 74 are mechanically parallel, i.e., each are subjected to the same linear displacement. In this manner, a displacement transducer depicted by the elements 56 and 57, is able to provide a readout signal which is indicative of stress in the sample as will be described hereinafter.

To achieve the mechanically parallel arrangement, both the spring 6 and the sample 74, illustrated as an elongated fiber, have one end of portion secured to a fixed member 70. Thus, the fiber 74 is secured between the fixed member 70 and the lower end of the shaft 38. The upper end of the shaft 38 contacts one end of the spring, in this case the center, the outer portions being fixed, and is directly linked therethrough to a weight table 48 by which various loads may be applied through the shaft 38 to sample 74. Since the sample 74 and the spring 6 are rigidly linked by the shaft 38, both undergo the same displacement depending upon the axial displacement of the shaft 38. Axial displacement of the shaft 38 is sensed by the displacement sensor 56 and applied to the y-axis or ordinate of an $x$-$y$ recorder 8. The sample is contained within an oven or other enclosure 78 whose temperature may be varied by a heater 17 controlled by a temperature programmer 7 of conventional design. The temperature within the chamber 78 is sensed by a suitable heat sensor or thermocouple 73 whose output is applied to the abscissa or x-axis of the x-y recorder 8.

The analyzer and its unique method of operation may perphaps be more readily understood mathematically. If F is used to represent the total load applied to the system via the weight tray 48, $F_1$ the resisting force of the spring 6, and $F_2$ the resisting force of the sample 74 then $$F = F_1 + F_2 \tag{1}$$

But according to Hooke's Law:
a. for the sample $$F_1 = K_1 \, \Delta s \tag{2}$$

where $K_1$ is the modulus of elasticity of the sample and $\Delta s$ is the axial displacement of the shaft 38.
b. for the spring $$F_2 = K_2 \, \Delta s \tag{3}$$

where $K_1$ is the modulus of elasticity of the spring.

Thus to measure say the stress relaxation in the sample, i.e., the stress decay at constant temperature and elongation as a function of time, the oven temperature is held constant and a known weight ($F$) is placed in the weight tray 48. Substituting equation (3) into equation (1) and solving for $F_1$ it is seen that $F_1 = F - K_2 \, \Delta s$. Since $F$ and $K_2$ are known and $\Delta s$ is measured it is seen that $\Delta s$ is a measure of stress in the sample.

Similarly if sample stress is to be measured as a function of temperature, no load is placed in the weight tray, hence $F = 0$ and $F_1 = - K_2 \, \Delta s$. Thus the displacement $\Delta s$ is a measure of stress in the sample under varying temperature conditions. Thus if the displacement signal is processed to represent $F_i$ or $F_i$ divided by sample cross-section area (stress) and plotted against thermocouple temperature, a stress-temperature plot is obtained. It may be seen from these equations that the modulus of elasticity $K_2$ reverses polarity in these two measurements.

Since the spring 6 is a passive device, its addition to the Du Pont thermomechanical analyzer converts the analyzer from a displacement sensing apparatus alone to an accurate reliable force or stress measuring device. Since the spring 6 is mechanically in parallel with the sample it does not require additional electronic processing or sensing and is not the source of noise, nor does it have a high failure rate. In the preferred embodiment of this invention, the apparatus illustrated in FIG. 3 is adapted to be used in conjunction with the apparatus of FIG. 2 which depicts the existing Du Pont thermomechanical analyzer.

Figure 2:
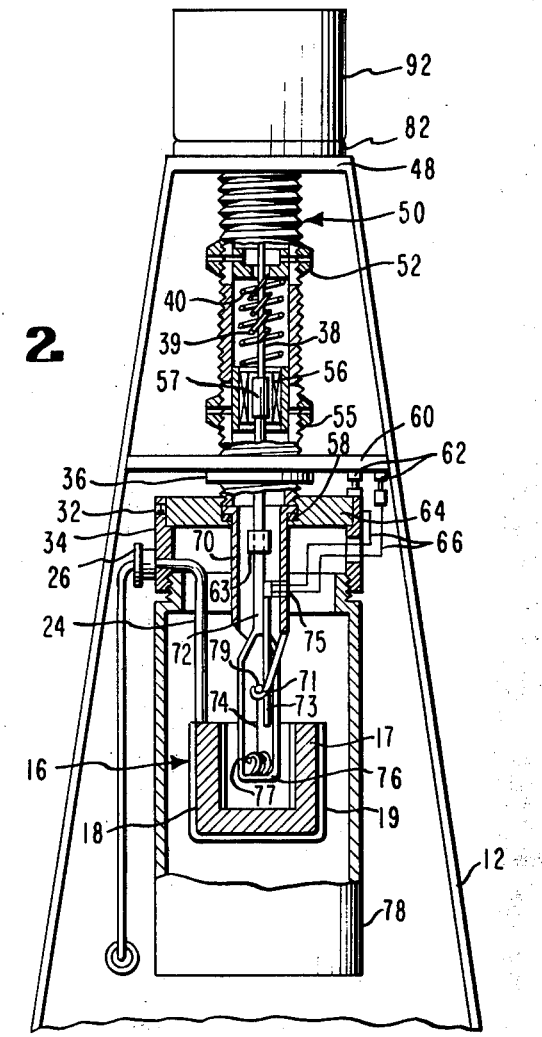
FIG. 2 is a fragmentary, partially cut away elevation view of a thermomechanical analyzer of the type described in the aforementioned Levy et al. patent modified in accordance with this invention to facilitate stress analysis of materials.

The thermomechanical analyzer illustrated in FIG. 2 comprises a base (not shown) having attached thereto rising support members 12. Affixed to the upper portions of the rising support members 12 are an upper horizontal support 48 and a lower horizontal support 60. The horizontal support members 48 and 60 have openings therein to receive an externally threaded, vertically positioned, tubular head assembly 50. The head assembly 50 is held securely in position by an upper sleeve 80 screwably fastened against the top of the upper horizontal support 48 and a lower retainer nut 36 screwably fastened against the bottom of the lower horizontal support 60. Any suitable material, for example, aluminum, can be used for construction of the supporting structure of the analyzer.

A shaft 38 constructed of any suitable nonmagnetic material, for example, a nonmagnetic stainless steel, is slideably positioned within the head assembly 50 and is suspended therein by an adjustable suspension mechanism comprising a small helical spring 39, connected to the shaft 38 and to a vertically adjustable position control nut, generally designated as 52.

Housed within the lower portion of the head assembly is an adjustable transducer, generally designated as 56, which translates vertical motion of the shaft 38 into an electrical output signal. The adjustable transducer 56 is a linear variable differential transformer. As described by Levy et al., the strength of the signal induced in the secondary windings of the alternating current (AC) input to the primary windings is a function of the position of the movable transformer core 57. The output of the transducer is typically connected to the y-axis of an x-y recorder. The transformer is adjustable vertically by an adjusting mechanism depicted by the nut 55. A compression spring 40 prevent movement, once adjustment is made, of the transformer and spring suspension 52.

An insulated flask assembly has three parts, an insulated flask 78, and a two-piece cap having an inner ring 64 and an outer ring 34. The inner ring 64 of the cap is screwably attached to the lower portion of the head assembly 50. The outer ring 34 is slideably fitted to the inner ring 64 and is secured thereto by a setscrew 32. The insulated flask 78 is in-turn screwably attached to the outer ring 34 of the cap. The flask assembly is of the Dewar type, and preferably is constructed of materials to withstand the operating temperatures of the analyzer, that is, from −250° to 1,000° C.

An annular sample holder 70 is made of material with a low coefficient of thermal expansion, preferably quartz. The upper lip of the sample holder is positioned in a circular recess in the top of the inner flask cap ring 64. A resilient washer 58 is placed between the upper lip of the sample holder 70 and the inner ring 64 to prevent damage to the sample holder 70 when the assembly is screwably fitted to the bottom portion of the head assembly 50. Thus, when the inner ring 64 is fastened to the head 50, the sample holder is intimately contacted with the head 50 and held firmly in that position by the resilient washer 58 and the inner cap ring 64.

The lower portion of the sample holder 70 is open with a hook 71 formed on one side with the hook itself being positioned along the axis of the shaft 38 so that a fiber loop may be looped over the hook. The second or lower hook, over which the sample fiber is looped, is provided by a replaceable bit 72 that may be housed in a chuck 63 at the lower end of shaft 38. The replaceable bit 72 has a stirrup 76 formed at its lower end. A lower hook 77 is formed on the horizontal portion of the stirrup.

Alternatively if both hooks 71 and 77 are formed to be double side by side hooks, the sample may be pinched in soft metal (such as aluminum) balls 79 in much the same manner as split shot is used as a fishing weight. In still other alternatives screw tightened grippers may be used.

A sample temperature measuring thermocouple is located in the lower region of the sample holder to assure the temperature of the sample as it is tested. The thermocouple leads 66 are enclosed in a quartz tube 73 having two interior channels. The quartz tube 73 is bonded or clipped to the inner wall of the sample holder. The thermocouple leads 66 exit the sample holder through two holes 75 in the sample holder and are attached to connectors 62 on the lower horizontal support member 60.

A bit 72 is coaxially positioned below the shaft 38 within the upper sample holder 70. The lower end of the bit 72 is located directly above the sample 76. The bit 72 is constructed of the same material as the sample holder 70, perferably quartz.

A cylindrical heater 16 with a self-contained control thermocouple is fitted around the lower portion of the sample holder 70 and bit 72. The heater may contain windings of resistance wire around a ceramic core or any other suitable construction. The windings are cemented into place. After the cement has been allowed to dry, the exterior surface of the wound ceramic core 18 is encased with a liquid-tight cover 19, the space between said cover and said core being filled with an insulating material.

The heater is held in position by tightening a nut 26 on the heater support arm 24 which locks it in position in a spot provided in the outer ring 34 of the cap.

Further, according to this invention, a sleeve 80 having a flange portion 82 is introduced into the bore 84 formed in the upper horizontal support 48 such that the tubular head assembly 50 is sturdily secured by the sleeve 80. The sleeve 80 has a central bore 89 to permit the passage of the shaft 38 therethrough into the interior of a carrier 92 which holds the elastic means or spring 6 (FIG. 1) attachment for the mechanical analyzer of FIG. 2. The shaft has a rounded tip portion 86. The shaft 38 is permitted to extend therethrough to contact the central portion of a flat or planar disc-like load cell 88. The load cell 88 is threaded into a central bore 90 of the carrier 92 whose lower portion has an internally threaded sleeve-like portion 94 which engages external threads of the sleeve 80.

In a preferred embodiment of the invention, the load cell 88 includes a pair of disc-like planar springs 96 which have a linear modulus of elasticity over the normal operating ranges of the instrument. Preferably, also, the passive load cell 88 is constructed in a sandwich assembly including annular discs 104 held together by screws 106 in which the springs 96 are held in parallel relationship. Springs of this type are commercially available from Statham Instruments, Oxnard, Calif. Such flat springs preferably have no offset and have a modulus of elasticity that can be varied by changing the thickness of the springs. The springs are separated by an armature 98 that spans the axial distance between the flat springs 96 such that an axial thrust produced by the shaft 38 acts equally upon both springs. The upper portion of the armature includes an upper shaft 100, whose upper portion has an (not shown) and internally threaded to facilitate the mounting of a weight tray 48 thereon. The weight tray is for calibration purposes and also for loading the sample in certain tests.

Figure 4:
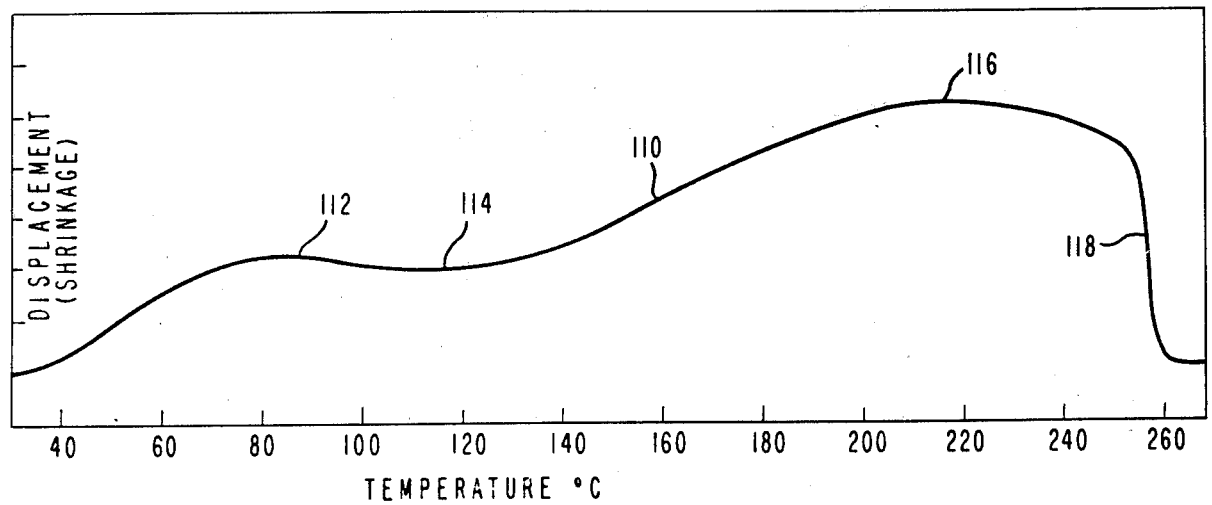
FIG. 4 is a typical plot of stress as a function of temperature in a plastic material when tested using the thermomechanical analyzer of this invention operated in a material tension mode.

In use the thermomechanical analyzer may be operated as previously described in connection with FIG. 1. In the fiber tension mode, a strand of fiber is placed on the hooks 71, 77. The displacement transducer or sensor 56 is positioned by suitable axial adjustment of the transformer along the shaft 38 until a zero condition is obtained. Next, the temperature programmer 7 (FIG. 1) is activated and the heater 16 tends to increase the temperature within the insulated flask 78. As is known, with the increase in temperature, shrinkage stresses occurring at various temperatures in the fiber or other sample material yield an output in recorder 8 (FIG. 1) as is typified in the plot 110 of FIG. 4. As may be observed, the displacement with temperature incurs a peak typified by the point 112. This peak is typical in characterizing the particular fiber under test. The location in temperature and the magnitude of these peaks are indicative of the polymeric material, process conditions and thermal history of the samples. With continued increase in temperature, the displacement and/or stress within the fiber decreases to a valley point 114, thereafter reaching a maximum stress 116 until the melting point of the fiber is reached and the stress within the fiber drops off as typified by the steeply sloped portion 118 until a zero point is reached. The spring constant $K_2$ of the flat springs in the passive load cell 88 are selected such that it is much greater than the typical spring constants $K_1$ for the fibers or materials under test. Thus the load cell acts as a force transducer yielding information as to fiber stress.

Figure 5:
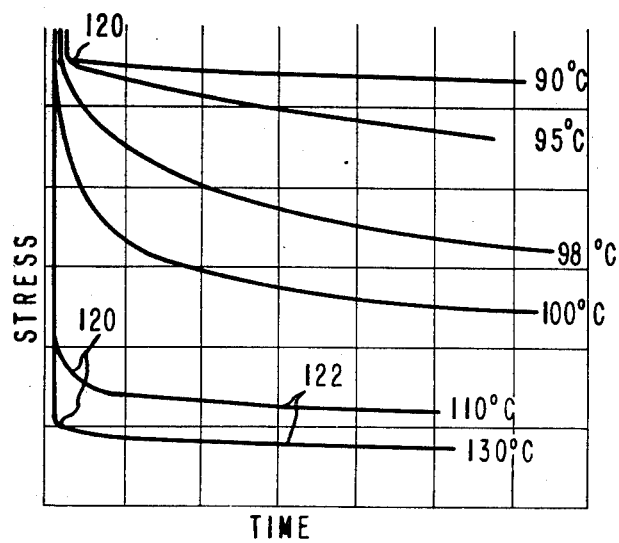
FIG. 5 is a typical plot of stress plotted as a function of time when the thermomechanical analyzer of this invention is operated in a stress relaxation mode.

The second primary mode of operation is the so-called stress relaxation mode as previously described which provides data equivalent to the test previously referred to in the ASTM D-2991-71. In this mode of operation the sample under test is placed on the stress hooks 71, 77 or grippers previously described and while the sample is held at various isothermal temperatures, the sample is subjected to various loads. The stress of the sample then is observed as a function of time at the various isothermal temperatures. An example of resultant stress as the ordinate and time as the abscissa is illustrated in the typical plot shown in FIG. 5. In this figure, the various curves are denoted by the temperatures 90°, 95°, 98°, 100°, 110°, and 130° C. In this instance, the test data is representative of a polyvinyl chloride (PVC) sample. Prior to running the test it is desirable that the scale be calibrated by placing varying weights on the weight tray 48 and observing the displacement on the ordinate or vertical axis. It will be observed in each instance that as the temperature increases, the stress that is retained within the sample decreases in a similar manner. It is to be noted, however, that in the middle temperature ranges between 98° and 100° C., the decay of stress occurs as a more gradual function of time rather than having a sharp knee as typified by the points designated 120. This gradual decrease of stress as a function of time typifies the passage of the sample through its glass transition temperature $T_g$. Initially, the sample is in its so-called glassy state during which it retains a high value of stress and then remains constant with little or no further decreases as a function of time. As it approaches the glass transition temperatures of 98°–100° C., the material becomes visco-elastic, hence the more gradual change. As it passes through the glass transition temperature, it becomes rubbery. This stage permits a very rapid stretching to a limit point after which the stress remains constant as typified by the portions 120 of the temperature curves 110–130. Various log/log plots and other determinations may be made using these curves in order to obtain a more precise determination of the glass transition temperature of the sample and other desired characteristics according to the information sought.

There has thus been described a relatively unique method and system wherein the stress of various sample materials may be readily ascertained. The system is one which utilizes a spring having a known spring constant connected mechanically in parallel with the sample under test such that each undergoes the same displacement under load (either internal or external to the sample). Using this unique system not only facilitates the utilization of a simpler apparatus, but permits the ready adaptation of an existing thermal materials analyzer incorporating a displacement sensor into a stress analyzer with a minimum of effort.

I claim:

1. A mechanical analyzer for measuring stress or tension in a sample material having a modulus of elasticity comprising:
    a flat spring having a known modulus of elasticity over the measuring range of said analyzer, said known modulus being greater than said sample modulus,
    coupling means for coupling said flat spring and said sample mechanically in parallel such that each are subjected to the same displacement, and
    transducer means for sensing said displacement.

2. The analyzer of claim 1 wherein said coupling means includes means for applying the same load directly to said sample and to said flat spring.

3. The analyzer of claim 2 which also includes means for varying the temperature of said samples as a function of time, and
    means for providing a signal indicative of the temperature of said sample.

4. The analyzer of claim 1 wherein said coupling means includes:
    a frame,
    a shaft slideably and axially positioned within said frame, said transducer means being responsive to the axial movement of said shaft, and
    mounting means to mechanically couple said sample in tension between said shaft and said frame, said flat spring being mechanically coupled between said shaft and said frame.

5. The analyzer of claim 4 which also includes means for varying the temperature of said sample as a function of time, and
    means for providing a signal indicative of the temperature of said sample.

6. The analyzer of claim 4 wherein said mounting means includes a coaxial member positioned coaxially about said shaft and secured to said frame, said member being adapted to engage a first portion of said sample, said shaft being adapted to engage a second portion of said sample.

7. The analyzer of claim 6 wherein said flat spring is a passive load cell having a planar disc-like spring,
    the central portion of said disc-like spring being contacted transversely of its plane by said shaft,
    the peripheral portion of said disc-like spring being secured to said frame.

8. The analyzer of claim 4 wherein said flat spring is a passive load cell having a planar disc-like spring,
    the central portion of said disc-like spring being contacted transversely of its plane by said shaft,
    the peripheral portion of said disc-like spring being secured to said frame.

9. In a thermomechanical sample analyzer for measuring stress or tension in a sample having a modulus of elasticity to be determined and having
    a frame,
    a head assembly mounted on said frame,
    a shaft slideably positioned in said head assembly,
    a transducer responsive to the axial displacement of said shaft for providing an output signal,
    a sample holder mounted on said frame and positioned in coaxial relation to said shaft, means for providing a signal indicative of sample termperature, and a heater having a hollow cylindrical core positioned in coaxial relation to said sample holder, the improvement comprising separate mounting means on said sample holder and one end of said shaft for positioning said sample in tension therebetween, and a flat spring having a known modulus of elasticity greater than said sample modulus, axially coupled between the other end of said shaft and said frame, whereby said flat spring and said sample are mechanically in parallel and the output signal from said transducer is related to stress in said sample.

10. A method of analyzing samples of materials using flat spring having a known modulus of elasticity greater than the modulus of elasticity of said samples comprising the steps of:

securing a first portion of said sample to a fixed reference point, securing a first portion of said spring to a fixed reference point, rigidly interconnecting a second portion of said sample different than said first portion and a second portion of said spring different than said first portion through a linkage such that they are mechanically in parallel and said sample is in tension, varying the temperature of said sample as a predetermined function of time, and sensing the displacment of said spring.

11. The method set forth in claim 10 which includes the additional steps of subjecting said sample and said spring to a load through said linkage.

* * * * *